United States Patent [19]

Pierre et al.

[11] 4,120,755

[45] Oct. 17, 1978

[54] KINETIC METHOD FOR DETERMINATION OF GLUCOSE CONCENTRATIONS WITH GLUCOSE DEHYDROGENASE

[75] Inventors: Kenneth J. Pierre; Ker-Kong Tung, both of Vista, Calif.

[73] Assignee: Beckman Instruments, Inc., Fullerton, Calif.

[21] Appl. No.: 791,825

[22] Filed: Apr. 28, 1977

[51] Int. Cl.$^2$ ............................................. G01N 31/14
[52] U.S. Cl. ............................................. 195/103.5 C
[58] Field of Search .................. 195/103.5 C, 103.5 R

[56] References Cited

U.S. PATENT DOCUMENTS 3,964,974  6/1972  Banauch et al. ............... 195/103.5 C

OTHER PUBLICATIONS

Banauch et al. Z. Klin. Chem. Klin. Biochem, vol. 3, pp. 101–107 (1975).
Lutz et al., Clin. Chem. 21: 1372–1377 (1975).
Lutz, Clin. Chem. 22: 929 (1976).
Rindfrey et al., Z. Anal. Chem. 279: 196 (1976).
Keller et al., J. Clin. Chem. Clin. Biochem 14: 27–30 (1976).
Pauley et al., Hoppe-Seyler's Z. Physiol. Chem. 356:1613–1623 (1975).

*Primary Examiner*—Lionel M. Shapiro
*Attorney, Agent, or Firm*—R. J. Steinmeyer; R. S. Frieman

[57] ABSTRACT

The range of linearity of the kinetic method for the determination of glucose concentrations using a reagent of the type comprising a buffer, a pyridine coenzyme, and glucose dehydrogenase, is significantly increased when the buffer employed in the reagent has a pH of from about 7.9 to about 9.0.

14 Claims, 1 Drawing Figure

KINETIC METHOD FOR DETERMINATION OF GLUCOSE CONCENTRATIONS WITH GLUCOSE DEHYDROGENASE

BACKGROUND OF THE INVENTION

1. Field of Invention

This invention pertains to reagents for use in the kinetic method for the determination of glucose with glucose dehydrogenase.

2. Description of the Prior Art

Kinetic methods for the determination of glucose concentrations in samples, e.g., body fluids, with glucose dehydrogenase are known. D. Banauch, W. Brummer, W. Ebeling, H. Metz, H. Rindfrey, H. Lang, K. Leybold and W. Rick, *Z. Klin. Chem. Klin. Biochem.*, 13:101 (1975), reported a kinetic method for determining glucose using glucose dehydrogenase. The reagent of Banauch et al. comprised 160 mmoles/l of tris buffer, pH 7.8, 0.6 U/ml glucose dehydrogenase, and 2.1 mmole/l NAD. This reagent, when employed in the kinetic method was stated to have yielded a calibration curve linear up to 1,000 mg/dl (the sample to reagent ratio was not specified).

Lutz et al., *Clinical Chemistry*, 21 (10):1372 (1975), also disclosed a kinetic method for the determination of glucose using the glucose dehydrogenase reaction. The glucose dehydrogenase reagent employed by Lutz et al. comprised 86.5 mg of NAD and 6 mg of glucose dehydrogenase in 50 ml of tris buffer (pH 7.8). Lutz et al. reported a deviation from linearity of their uncorrected glucose dehydrogenase method as being 4% at 300 mg%, 8% at 500 mg% and 19% at 1000 mg% using a sample to reagent ratio of 1:41. Based upon their work, Lutz et al. concluded that "(i)t therefore seems impossible to reach the linearity claimed by others (Banauch et al., supra)."

Lutz, *Clinical Chemistry*, 22(6):929 (1976), disclosed an attempt to improve the linearity of the kinetic method for determination of glucose by adding competitive inhibitors for GDH to the enzymatic reagent in order to increase the linearity of the reaction. Using an equation to correct for nonlinearity, Lutz was only able to increase the range of linearity to about 500 mg/dl using a sample to reagent ratio of 1:41.

H. Rindfrey, R. Helger and H. Lang, *Kinetic Glucose Determination with Glucose Dehydrogenase*, *Z. Anal. Chem.*, 279:196 (1976), subsequently confirmed Lutz et al.'s allegation that the Banauch et al. article's statement as to the range of linearity was erroneous. Rindfrey et al. disclosed that the kinetic glucose determination with glucose dehydrogenase was linear up to 300 mg/dl and that at 500 mg/dl the error was −10%. (The sample to reagent ratio employed was 1:50.)

SUMMARY OF THE INVENTION

This invention encompasses a kinetic glucose reagent of the type comprising a buffer, a pyridine coenzyme, and glucose dehydrogenase, characterized in that said buffer has a pH of from about 7.9 to about 9.0. By using this improved kinetic glucose reagent in a kinetic glucose determination, the range of linearity is extended from the prior art limit of about 300–500 mg/dl to about 1200 mg/dl (at a sample to reagent ratio of 1:41).

DESCRIPTION OF THE PREFERRED EMBODIMENTS

Figure 1:
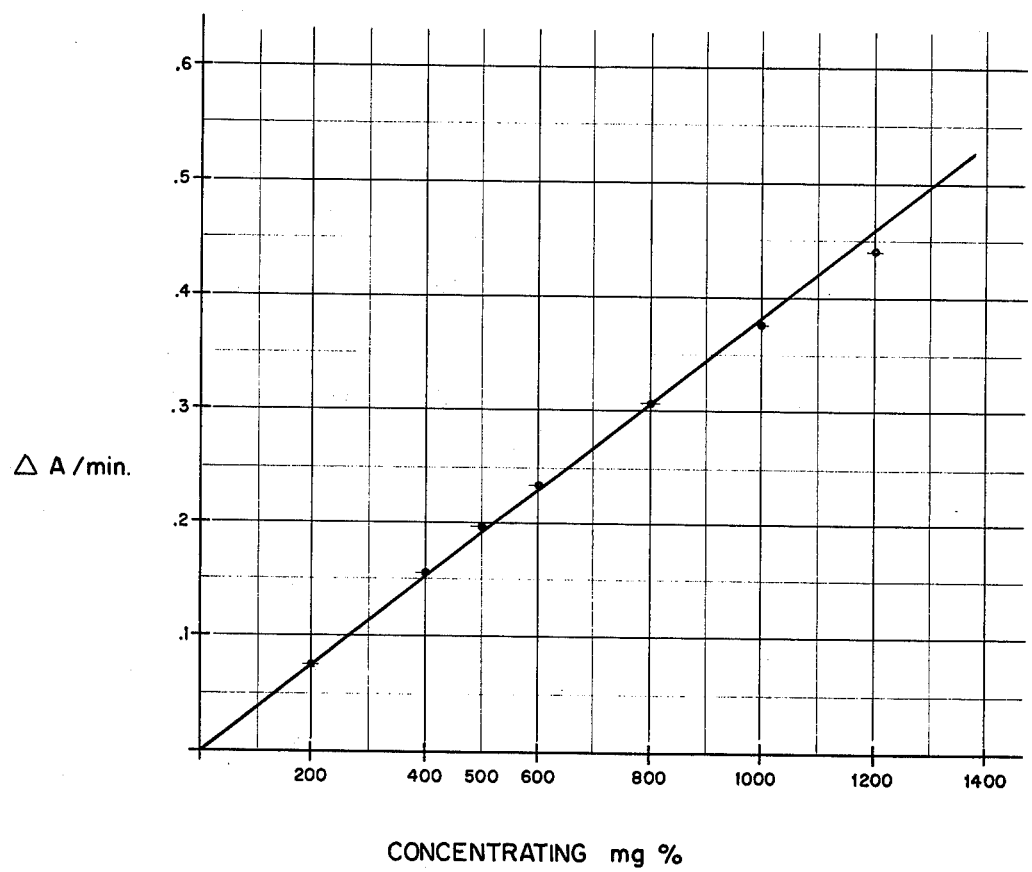
FIG. 1 is a plot of ΔA/min glucose substrate concentration obtained using the improved reagent of the instant invention.

The improved kinetic glucose reagent of the instant invention is employed in a kinetic assay for measuring the glucose content of a sample, e.g., biological fluid such as blood serum and urine. The kinetic assay is based on the following reaction I:

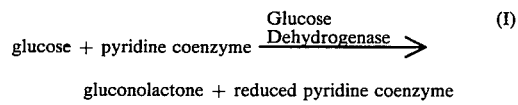

gluconolactone + reduced pyridine coenzyme

The concentration of glucose in the sample is determined by measuring the rate of increase of absorbance associated with the production of reduced pyridine coenzyme which is a measure of the concentration of glucose.

According to the present invention, it is essential that the amount of glucose to be assayed be rate-limiting. Thus, the amount of the various constituents of the kinetic glucose reagent of the instant invention should be present in suitable amounts to ensure that the observed reaction rate for reaction I, supra, is characteristic of and determined by the concentration of glucose in the sample.

The reagent of the instant invention comprises a buffer having a pH of from about 7.9 to 9.0, a pyridine coenzyme, and glucose dehydrogenase. The buffer preferably has a pH of about 8.0 to about 8.5 and more preferably has a pH of about 8.2. Any buffer which is compatible with the other ingredients of the reagent and which has a pH within the desired range can be used. Exemplary buffers include triethanolamine, sodium 5:5-diethyl-barbiturate, tri (hydroxymethyl) aminomethane, diethanolamine and phosphate buffers. Phosphate buffers are the preferred buffers for use in the instant invention. Exemplary phosphate buffers include potassium phosphate and sodium phosphate buffers. Although the exact amount of buffer employed is not critical, it is preferred that said buffer be present in an amount from about 0.1 to 1 mole, and more preferably about 0.5 mole, per liter of reagent.

The pyridine coenzyme or coenzymes contained in the kinetic reagent of this invention is preferably nicotinamide adenine dinucleotide (NAD) or nicotinamide adenine dinucleotide phosphate (NADP), especially NAD. Other suitable pyridine coenzymes are, for example, thio-NAD, thio-NADP, nicotinamide purine dinucleotide, nicotinamide-(6-methyl-purine)-dinucleotide or nicotinamide-(2-chloro-6-methyl-purine)-dinucleotide. The exact concentration of the pyridine coenzyme is not critical so long as the glucose in the sample to be assayed is rate-limiting. However, it is preferred that said coenzyme be present in amounts from about 0.001 to about 0.025 moles and, more preferably, about 0.0027 moles, per liter of reagent.

The glucose dehydrogenase employed in this invention can be produced from microorganisms. Preferably, the glucose dehydrogenase is produced from a *Bacillus Megaterium* or a *Bacillus Cereus* microbial source. The exact amount of glucose dehydrogenase employed in the kinetic glucose reagent of the instant invention is not critical so long as the glucose in the sample to be assayed is rate-limiting. However, it is preferred that the glucose dehydrogenase be present in an amount from about 100 to about 3000 International Units (IU) per liter (l) of reagent. The more preferred amount of glucose dehydrogenase will vary depending on the sample to reagent ratio but will usually fall within the range of from about 300 to about 2000 IU/l. About 1600 IU/l of glucose dehydrogenase is optimal.

Although the ionic strength of the reagent is not critical, in order to increase the thermal stability of glucose dehydrogenase it is preferred that the reagent of the instant invention have an ionic strength of from about 0.5 to about 7 M and more preferably from about 2 to about 4 M. Any salt which is compatible with the other ingredients of the reagent can be employed to adjust the ionic strength of the reagent. Exemplary salts include alkali chloride salts, such as, for example, lithium, sodium, and potassium chloride; potassium phosphate; sodium phosphate; ammonium phosphate; and mixtures thereof. Potassium chloride is the preferred salt.

It is also preferred that the kinetic glucose reagent of this invention contain (ethylenedinitrile)tetraacetic acid (EDTA). The exact amount of EDTA present is not critical but is preferably from about 0 to about 0.02 moles, and more preferably about 0.005 moles, per liter of reagent.

The reagent system of the present invention can be stored in the form of an aqueous solution or the solution can be freeze dried by conventional means and reconstituted with water when ready for use. The reagent system can also be prepared using the constituents thereof in powdered form which are solubilized with ready for use.

The measurement of the rate of reduced pyridine enzyme production and the conversion of such rate into the concentration of glucose can be accomplished by known methods. One such method uses spectrophotometric means to measure the change in absorbance of light due to the production of reduced pyridine coenzyme at wavelengths of from about 300 to about 370 nm at a temperature of from about 15° to about 50° C. A wavelength of about 340 nm at a temperature of about 25° to about 37° C. is preferred.

One convenient procedure for measuring the glucose content of a sample with the enzyme reagent of the instant invention is as follows:

| SYSTEM PARAMETERS | |
|---|---|
| Wavelength (λ) | 340 nm |
| Incubation Temperature | 30° to 37° C. |
| Mode | Absorbance |
| Absorbance range | 0 to 2 A |
| Cuvette pathlength | 1.0 cm |
| Total reaction time | Approximately 980 secs. |
| Reagent to sample ratio | Approximately 41:1 or higher |

PROCEDURE

1. Use glucose standard solutions at 50 mg/dl, 150 mg/dl, 300 mg/dl, and 600 mg/dl to prepare a standard curve as follows:

a. Into each appropriately marked cuvettes pipet 1.0 ml of a reagent within the scope of this invention and equilibrate at 30° or 37° C.

b. At a precise time, add 25 μl of the first standard to the appropriate cuvette, cover with parafilm and mix by gentle inversion. Exactly 30 seconds after addition of the standard, read and record absorbance at 340 nm in a properly zeroed spectrophotometer. This is $A_{30}$. Allow the reaction to proceed at the chosen temperature for another 60 seconds. Read and record absorbance at 340 nm exactly 90 seconds after addition of the standard. This is $A_{90}$. Determine the change in absorbance for the 60 second reaction period:

$$\Delta A/60 \text{ sec.} = A_{90} - A_{30}$$

c. In the same manner, assay all standard solutions, determining ΔA/60 sec. for each standard.

d. Prepare a standard curve by plotting the values obtained for ΔA/60 sec. against the known glucose concentration of the standard solutions used.

2. Assay all samples to be tested in the same manner as the standard solutions, determining ΔA/60 sec. for each sample.

CALCULATION

Compute glucose levels as follows:

The ΔA/60 obtained in Step 2 is used to read glucose concentration in mg/dl directly from the standard curve.

$$\text{Concentration of Unknown (mg/dl)} = \Delta A/_{60}\text{Unknown} \times \frac{\text{Conc. of Standard}}{\Delta A/_{60} \text{Standard}}$$

The following examples are provided for the purpose of further illustration only and are not intended to be limitations on the disclosed invention.

EXAMPLE I

The following is the composition of the preferred reagent of the instant invention:

| Ingredients | Optimal Conc. | Preferred Conc. Range |
|---|---|---|
| Buffer | | |
|   K$_2$HPO$_4$ | 0.5 M | 0.1 - 1 M |
|   KH$_2$PO$_4$ | | |
| Alkali Chloride | | |
|   KCl | 0.5 M | 0.1 - 1 M |
| EDTA | 0.005 M | 0 - 0.02 M |
| Pyridine Coenzyme | | |
|   NAD | 0.0027 M | 0.001 - 0.025 M |
| Glucose Dehydrogenase | 1600 IU/l | 100 - 3000 IU/l |
| pH | | |

The pH is preferably adjusted to about 8.0 to 8.5 and is more preferably 8.2.

EXAMPLE 2

A 5000 mg% glucose standard was prepared and allowed to stand overnight at room temperature. By diluting this standard a series of samples having known concentrations were obtained.

Into a cuvette was pipeted 1.0 ml of the optimal reagent of Example 1. The cuvette was then placed in a water bath and allowed to equilibrate at 37° C. Into the cuvette was then placed 25 μl of a sample containing a known amount of glucose. The reaction was run on a Beckman ® Model 25 brand spectrophotometer. The slope was continuously taken between 30 and 90 seconds with a recorder and a reading of the slope was obtained to get ΔA/min. This procedure was employed in assaying each of the samples containing a known concentration of glucose and the data obtained therefrom is tabulated in Table I and plotted in FIG. 1. An examination of FIG. 1 shows that by running a glucose assay employing a glucose dehydrogenase containing reagent, one is able to obtain a linearity of about 1200 mg% at a dilution (sample to reagent ratio) of 1:41.

Table II compares the linearity of the improved method of the instant invention with the linearity of prior art methods.

TABLE I

| Linearity for Glucose-Dehydrogenase Reagent at pH 8.2 | |
|---|---|
| Concentration of Glucose, mg% | ΔA/min, 60–90 sec. |
| 200 | 0.077 |
| 400 | 0.152 |
| 500 | 0.190 |
| 600 | 0.232 |
| 800 | 0.303 |
| 1000 | 0.371 |
| 1200 | 0.441 |
| 1500 | 0.521 |
| 1800 | 0.631 |
| 2000 | 0.682 |
| 2500 | 0.804 |
| 3000 | 0.940 |

TABLE II

| pH | Sample/Reagent | Linearity | Final Concentration mg% | Reference |
|---|---|---|---|---|
| 7.8 | Not specified | 1000 mg% | Not specified | J. Clin. Chem. Clin. Biochem. 13, 101 (1975) Banauch, Brummer, Ebeling, Metz, Tindfrey, Lang, Leybold and Rick |
| 7.8 | 1:41 | ~300 mg% | 7.3 | Clin. Chem. 21, 1372–1377 (1975) Lutz and Fluderger |
| 7.6 | 1:265 | 500 mg% | 1.9 | J. Clin. Chem. Clin. Biochem. 14, 27–30 (1976) Keller, Wolf, Faust, Bleicher and Becker |
| 7.8 | 1:50 | 300 mg% | 6 | Z. Anal. Chem. 279, 169 (1976) Rindfrey, Helger and Lang |
| 7.8 | 1:41 | 500 mg% | 12.2 | Clin. Chem. 22, 929 (1976) Lutz |
| 8.2 | 1:41 | 1200 mg% | 29.3 | Instant invention |

As is clear from an examination of Table II, the instant invention significantly increases the range of linearity of a glucose assay employing a glucose dehydrogenase containing reagent. The column of Table II entitled "Final Concentration" clearly shows that one employing the method and reagent of the instant invention is now able to accurately measure the amount of glucose present in a sample having a glucose concentration over two times greater than samples capable of accurate measurement with prior art methods and reagents.

Based on this disclosure, many other modifications and ramifications will naturally suggest themselves to those skilled in the art. These are intended to be comprehended as within the scope of this invention.

The embodiments of the invention in which an exclusive property of privilege is claimed are defined as follows:

1. A kinetic glucose reagent of the type comprising a buffer, a pyridine coenzyme, and glucose dehydrogenase, characterized in that said buffer has a pH of from about 7.9 to about 9.0.

2. The kinetic glucose reagent of claim 1 wherein said buffer has a pH of from about 8.0 to about 8.5.

3. The kinetic glucose reagent of claim 2 wherin said buffer is selected from a group consisting of triethanolamine sodium 5:5-diethylbarbiturate-HCl, tris(hydroxymethyl) aminomethane, diethanolamine, and phosphate buffers.

4. The kinetic glucose reagent of claim 2 wherein said buffer is a phosphate buffer selected from a group consisting of potassium phosphate and sodium phosphate.

5. The kinetic glucose reagent of claim 2 wherein said buffer has a pH of about 8.2.

6. The kinetic glucose reagent of claim 5 wherein said buffer is selected from a group consisting of triethanolamine sodium 5:5-diethylbarbiturate-HCl, tris(hydroxymethyl) aminomethane, diethanolamine, and phosphate buffers.

7. The kinetic glucose reagent of claim 5 wherein said buffer is a phosphate buffer selected from a group consisting of potassium phosphate and sodium phosphate.

8. The kinetic glucose reagent of claim 1 wherein said buffer is selected from a group consisting of triethanolamine sodium 5:5-diethylbarbiturate-HCl, tris(hydroxymethyl) aminomethane, diethanolamine, and phosphate buffers.

9. The kinetic glucose reagent of claim 1 wherein said buffer is a phosphate buffer selected from a group consisting of potassium phosphate and sodium phosphate.

10. The kinetic glucose reagent of claim 1 comprising per liter of reagent:
(a) from about 0.1 to about 1 mole of said buffer;
(b) from about 0.1 to about 1 mole of an alkali chloride;
(c) from about 0 to about 0.02 mole of EDTA;
(d) from about 0.001 to about 0.025 mole of said pyridine coenzyme; and
(e) from about 100 to about 3000 International Units of glucose dehydrogenase.

11. The kinetic glucose reagent of claim 10 comprising per liter of reagent:
(a) about 0.5 mole of said buffer;
(b) about 0.5 mole of said alkali chloride;
(c) about 0.005 mole of EDTA;
(d) about 0.0027 mole of said pyridine coenzyme; and
(e) about 1600 International Units of glucose dehydrogenase.

12. An improved kinetic assay of the type employing a kinetic glucose reagent comprising a buffer, a pyridine coenzyme and glucose dehydrogenase, wherein the improvement comprises conducting said assay at a pH of from about 7.9 to about 9.0.

13. The kinetic assay of claim 12 wherein said assay is conducted at a pH at from about 8.0 to about 8.5.

14. The kinetic assay of claim 13 wherein said assay is conducted at a pH of about 8.2.

* * * * *